(12) United States Patent
Marsh et al.

(10) Patent No.: US 10,722,657 B2
(45) Date of Patent: Jul. 28, 2020

(54) METHOD FOR ASSEMBLING A DRUG DELIVERY DEVICE AND DRUG DELIVERY DEVICE

(71) Applicant: Sanofi, Paris (FR)

(72) Inventors: William Geoffrey Arthur Marsh, Buckinghamshire (GB); Anthony Paul Morris, West Midlands (GB); Mike Cameron Bainton, Kineton (GB); Matthew Meredith Jones, Warwick (GB)

(73) Assignee: Sanofi, Paris (FR)

( * ) Notice: Subject to any disclaimer, the term of this patent is extended or adjusted under 35 U.S.C. 154(b) by 311 days.

(21) Appl. No.: 15/533,282

(22) PCT Filed: Dec. 8, 2015

(86) PCT No.: PCT/EP2015/078901
§ 371 (c)(1),
(2) Date: Jun. 5, 2017

(87) PCT Pub. No.: WO2016/091840
PCT Pub. Date: Jun. 16, 2016

(65) Prior Publication Data
US 2018/0008782 A1 Jan. 11, 2018

(30) Foreign Application Priority Data
Dec. 8, 2014 (EP) .................................... 14306960

(51) Int. Cl.
*A61M 5/315* (2006.01)
*A61M 5/20* (2006.01)
(Continued)

(52) U.S. Cl.
CPC ...... *A61M 5/31541* (2013.01); *A61M 5/2033* (2013.01); *A61M 5/24* (2013.01);
(Continued)

(58) Field of Classification Search
CPC .. A61M 5/31553; A61M 5/20; A61M 5/1454; A61M 2205/583;
(Continued)

(56) References Cited

U.S. PATENT DOCUMENTS 5,261,882 A * 11/1993 Sealfon ............... A61M 5/1454
128/DIG. 12
2012/0283659 A1 11/2012 Kouyoumjian et al.

FOREIGN PATENT DOCUMENTS

EP 2482899 8/2012
WO WO 2008/142394 11/2008
(Continued)

OTHER PUBLICATIONS

International Preliminary Report on Patentability in International Application No. PCT/EP2015/078901, dated Jun. 13, 2017, 7 pages.
(Continued)

*Primary Examiner* — Bhisma Mehta
*Assistant Examiner* — Hamza A Darb
(74) *Attorney, Agent, or Firm* — Fish & Richardson P.C.

(57) ABSTRACT

A method for assembling a drug delivery device that includes mounting a cartridge with a bung, the mechanism, the plunger and the spring within a housing such that a spring biases a plunger in a dispensing direction and that a drum and/or the release member is attached to the plunger attaching a tool with torque measurement capability to the drum or a release member of a dose mechanism in a state where at least one housing part is detached from further housing part; setting a dose by rotating the dose setting member in a first direction, activating a trigger and monitoring the torque applied to the drum or the release member; releasing the trigger upon detection of a predetermined change in the torque measured by the tool; and releasing the tool and closing the housing.

9 Claims, 9 Drawing Sheets

(51) Int. Cl.
*A61M 5/31* (2006.01)
*A61M 5/24* (2006.01)
*A61M 5/28* (2006.01)

(52) U.S. Cl.
CPC ............ *A61M 5/2455* (2013.01); *A61M 5/28* (2013.01); *A61M 5/3146* (2013.01); *A61M 5/3157* (2013.01); *A61M 5/31501* (2013.01); *A61M 5/31553* (2013.01); *A61M 2005/31518* (2013.01); *A61M 2205/332* (2013.01); *A61M 2205/581* (2013.01); *A61M 2205/582* (2013.01); *A61M 2205/585* (2013.01); *A61M 2207/00* (2013.01)

(58) Field of Classification Search
CPC ........... A61M 2005/31518; A61M 2005/3126; A61M 2205/581; A61M 2205/585; A61M 5/31563; A61M 5/31541; A61M 5/2033; A61M 5/2455; A61M 2205/332; A61M 5/31501; A61M 5/3157; A61M 5/3146; A61M 5/28; A61M 5/24; A61M 2207/00
See application file for complete search history.

(56) References Cited

FOREIGN PATENT DOCUMENTS

| | | |
|---|---|---|
| WO | WO 2010/112377 | 10/2010 |
| WO | WO 2011/039229 | 4/2011 |
| WO | WO 2011/039233 | 4/2011 |
| WO | WO 2011/121061 | 10/2011 |
| WO | WO 2014/029682 | 2/2014 |
| WO | WO 2014/036239 | 3/2014 |
| WO | WO 2014/139918 | 9/2014 |
| WO | WO 2014/166888 | 10/2014 |
| WO | WO 2014/166905 | 10/2014 |
| WO | WO 2016/091840 | 6/2016 |

OTHER PUBLICATIONS

International Search Report and Written Opinion in International Application No. PCT/EP2015/078901, dated Feb. 16, 2016, 10 pages.

* cited by examiner

Figure 21a
Figure 21b
Figure 21c
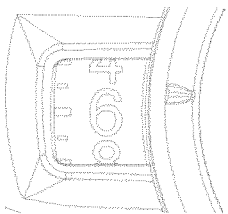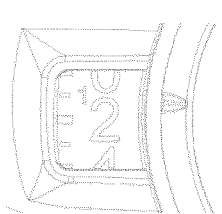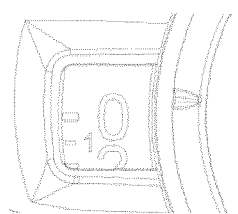
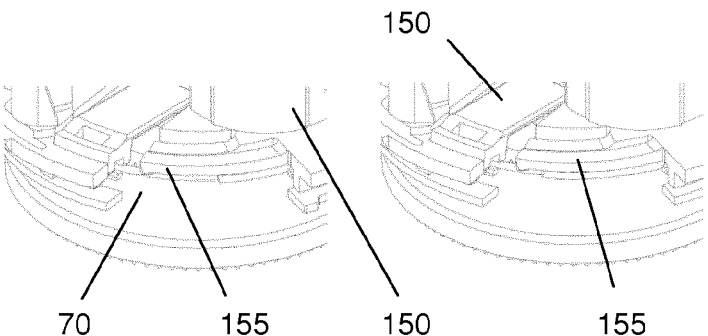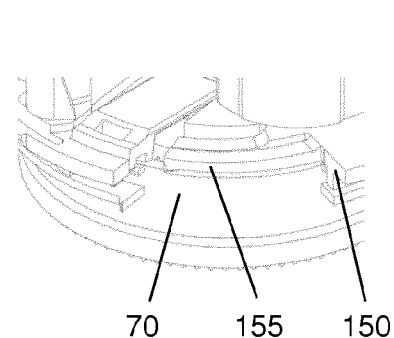
Figure 22a
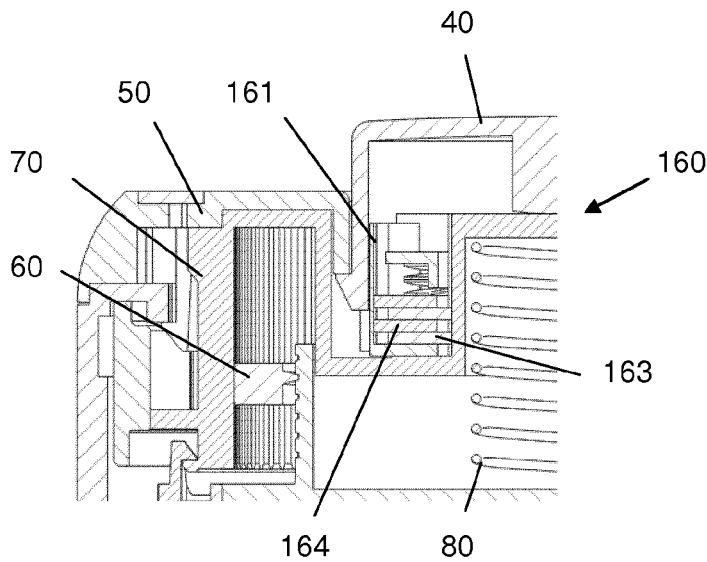
Figure 22b
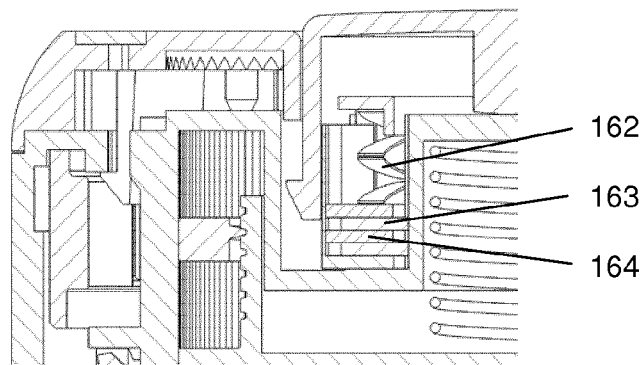

METHOD FOR ASSEMBLING A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2015/078901, filed Dec. 8, 2015, which claims priority to European Patent Application No. 14306960.7, filed Dec. 8, 2014, the entire contents of which are incorporated herein by reference.

TECHNICAL FIELD

The present disclosure is generally directed to a drug delivery device and a method for assembling same or its component parts. The drug delivery device may be a handheld injection device, i.e. a drug delivery device for selecting and dispensing a number of user variable doses of a medicament.

BACKGROUND

Drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable drug delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is in general applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. Further types of energy storage may comprise compressed fluids or electrically driven devices with a battery or the like. Although many aspects of the present disclosure are applicable for all of these types of devices, i.e. for devices with or without a drive spring or the like energy storage, the preferred embodiments require some kind of energy storage.

These types of delivery devices generally comprise of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the device that is used to set (select) a dose. During an injection, a plunger, spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

In known drug delivery devices, there may be an internal gap between parts of the drug delivery device after assembly which have to contact each other to ensure the delivery of the correct amount of the dose. The gap may be located between parts of the drive mechanism or between a part of the drive mechanism and e.g. the cartridge. This gap is a consequence of the tolerances associated with all the assembled parts and the requirement not to apply an undesirably high preload on the bung axially in the assembled drug delivery device, because too much preload would pressurize the drug in the cartridge and may cause it to leak, or may cause creep damage to plastic parts if they are loaded for significant periods of time during storage.

In a conventional drug delivery device, a priming operation is performed to ensure that the parts of the driving mechanism are moved to their predetermined position with respect to the other parts. Typically, the priming step has to be performed prior to the first use of the device to close a possible gap between the cartridge bung and the plunger and to overcome tolerances within the device. For the priming step, a user has to set a small dose and to dispense this dose while monitoring whether e.g. fluid leaves the device. This action has to be repeated until e.g. fluid actually leaves the device.

There is a risk of an underdose at least during the first use of the device if a user does not perform this priming step. Users who are unfamiliar with such drug delivery devices may fail to correctly prime their drug delivery device before dispensing the first dose. If this occurs, the correct volume of the drug may not be delivered in the first dose, as part of the dialed dose is needed to close up any gaps between parts in the mechanism.

EP 2 482 899 B1 discloses a manually operated drug delivery device with an assembly which can be adjusted during assembly of the device, preferably during final assembly after fitting the cartridge, to bring a piston rod in contact with a cartridge bung. This removes tolerance gaps from the assembly and eliminates the need for a priming operation which is undertaken by the user prior to delivery the first dose of drug. The assembly of this known device requires using a tool to move a first drive member with respect to a second drive member, thereby moving a piston rod towards a bung during an assembly action, and thereafter coupling the first drive member with the second drive member so that the movement of the first drive member with respect to the second drive member is prevented during a dose setting and delivery action.

WO 2014/036239 A2, WO 2010/112377 A1 and WO 2008/142394 A1 each disclose a drug delivery device comprising a spring loaded piston which is attached to a belt or tether retaining the piston against the force of the spring. One end of the belt is attached to a spool on a gear wheel which is in engagement with a worm gear driven by an electric motor. Actuation of the motor allows unwinding of the belt which in turn allows displacement of the piston by the spring. In addition, WO 2014/036239 A2 mentions a control unit with a sensor detecting slack in the belt or tether. Further a sensor and an encoder may be used to provide positional feedback, end-of-dose signal and error indication.

WO 2014/139918 A1 and WO 2011/039229 A1 each describe an assembly method for a drug delivery device, wherein the device comprises a threaded piston rod engaging a threaded drive sleeve. During assembly the drive sleeve is rotated thereby advancing the piston rod. The torque required for rotating the piston rod is measured to detect a sudden increase in torque when the piston rod contacts a bung in a cartridge. WO 2014/029682 A2 proposes a method for detecting snap engagement of a piston rod and a bung by a sudden change in force or torque required for piston rod displacement.

SUMMARY

The present invention is not directed to so called fixed dose devices which only allow dispensing of a predefined dose without the possibility to increase or decrease the set dose.

The present disclosure provides an assembly method and an alternative drug delivery device eliminating the risk of underdose during the first use of the device. It is a further object to improve user friendliness and handling of the device.

The disclosure is based on the idea that in a drug delivery device a spring applies a torque or force in a direction to move a bung in a cartridge. A release member controls the release of the spring force or torque. As the release member is released during manufacture to move e.g. a bearing face towards the bung, the torque or force on the release member (or a component part coupled thereto) is monitored. When the bearing face contacts the bung, the monitored torque or force changes and the release of the release member may be stopped. In other words, contact between the bearing face and the bung may be detected by detecting a change in the force or torque reacted by the release member (or a component part coupled thereto) which is reduced as soon as at least a part of this force or torque is reacted by the cartridge bung.

A method for assembling a drug delivery device or components thereof comprises the following steps:
i) providing a cartridge with a bung, a plunger, a spring biasing the plunger towards the bung and a release member coupled to the spring such that release of the spring is controlled by the release member,
ii) providing an instrument for measuring the torque or force of the spring reacted by the release member,
iii) releasing the spring, preferably by movement of the release member, while monitoring the torque or force by the measuring instrument,
iv) stopping the release member upon detection of a predetermined change in the torque or force measured by the measuring instrument.

In more detail, this method may comprise the steps:
a) providing a housing, e.g. with at least two housing parts, a dose setting and dispensing mechanism comprising at least a dose setting member, a release button or trigger, a release member and/or a drum, a plunger and a strained pressure spring,
b) mounting a cartridge with a bung, the dose setting and dispensing mechanism, the plunger and the spring within the housing such that the spring biases the plunger in a dispensing direction and that the drum and/or the release member is attached to the plunger,
c) attaching a tool with torque measurement capability to the drum or the release member of the dose setting and dispensing mechanism in a state where the drum or the release member is accessible from outside the housing, e.g. when at least one housing part is detached from the further housing part(s),
d) setting a dose by rotating the dose setting member in a first direction, activating the release button or trigger and monitoring the torque applied to the drum or the release member,
e) releasing the release button or trigger upon detection of a predetermined change in the torque measured by the tool,
f) releasing the tool from the drum or the release member and optionally closing the housing by attaching the at least one housing part to the further housing part(s).

In other words, an operation similar to the priming step usually required for known devices takes place already during assembly of the device. This not only reduces the risk of malfunctions but also facilitates use of the device. Due to the fact that the spring drives the plunger which in turn is attached to the drum and/or the release member, the spring exerts a torque to the drum and/or the release member. As soon as the plunger contacts the cartridge bung, this torque decreases due to the reaction force of the bung. This allows stopping the movement of the plunger towards the bung as soon as the plunger abuts the bung, but prior to exerting an undesirable high preload on the bung, i.e. without significantly pressurizing the drug in the cartridge. In addition, unlike the conventional priming step, it is not required to dispense drug from the cartridge. The operation similar to the priming step is performed using the spring and the dose setting and dispensing mechanism of the device. Thus, no additional component parts or functionalities are required for this operation, which keeps the device simple and robust and avoids time-consuming additional assembly steps.

Theoretically part of the release gear could be accessible without removing the housing, e.g. if the axis of the release gear is accessible through the body and if it contains a feature such as a hexagon head that can be rotated by the assembly tool. Alternatively, the cartridge holder could contain a hinged panel that is left open to 'prime' the device before being closed. As a further alternative, the housing, which may comprise several housing parts, is not fully assembled during the process of bringing the plunger (or the like drive mechanism component) into contact with the cartridge bung. Thus this process may be integrated in the assembly of the device not requiring that the device is opened to perform this step.

The plunger is preferably attached to the drum and/or the release member such that the spring which acts on the plunger causes a rotation of the drum and/or the release member, i.e. a torque is generated by the spring. This may include the use of a torsion spring, however, the use of a compression spring is preferred. As an alternative to the measurement and detection of a torque by the tool, a force acting on the drum and/or the release member may be measured and detected.

The housing may comprise a main body part and a cartridge holder part. The cartridge holder part may comprise a cartridge retaining part and a rear part. Further, a chassis may be provided constrained within the main body part. To allow access to the drum and/or release member by the tool during assembly, it is preferred to assemble the whole device except the rear part of the cartridge holder. Thus, the device has its full functionality as during normal use but it is possible to attach the tool to the drum and/or release member. After the plunger has been moved to abut the bung, the rear part of the cartridge holder may be closed, too, to finalize assembly.

It may be desirable to deliver the device in a condition without any dose set, i.e. in a zero dose position. For this purpose, the dose setting member is rotated in a second direction, which is opposite to the first direction after the release button or trigger is released. This cancels any remaining set dose without dispensing drug.

The dose set during step d) is preferably chosen according to the expected size of the gap between the plunger and the cartridge bung. For example, a dose of 10 IU (international units of insulin formulation) may be set in step d). However, if in step d) the predetermined change in the torque is not detected, the release button or trigger is preferably released after the plunger moved in the dispensing direction a distance corresponding to the dose set in step d) and step d) may be repeated.

While it is preferred that the predetermined change in the torque is a rapid decrease in torque due to the plunger contacting the bung in the cartridge, further significant changes in torque (or a force) may be used for detecting a desired position of the plunger with respect to the bung, too.

The above object is further solved with a drug delivery device assembled by the above method. The device comprises the housing having a longitudinal axis defined by a compartment for receiving the cartridge containing a medicament, the plunger suitable for acting on the bung of the cartridge retained in the housing, the strained pressure spring arranged between the housing and the plunger, a retaining member coupled to the plunger, and a release member operable between a first state, in which the release member constrains the retaining member to the housing, thus preventing movement of the plunger, and a second state, in which the release member is movable relative to the housing, thus allowing movement of the plunger by means of the spring. Due to the priming-like operation during assembly, the plunger abuts the bung in an unused delivery state of the device. In other words, priming is no longer necessary because when the device is given to a user for the first use, the bung and the bearing are already in contact with each other. According to the disclosure, the unused delivery state of the device shall mean the state of the device as it is sold and delivered to customers. Typically, this is the state in which a user takes the device out of its packaging. Thus, the device is ready to use, which eliminates the requirement of a priming step prior to the first use.

The present disclosure is further based on the idea to provide a power reservoir applying an axial load on the plunger which acts on the cartridge bung. To avoid uncontrolled dispensing from the cartridge, the retaining member is provided which is coupled to the plunger to hold the plunger against the force of the power reservoir. The release member which is coupled to the retaining member allows movement of the retaining member and, thus, the plunger for a desired distance corresponding to the dose to be dispensed. In other words, a tensile load acts on the retaining member under the action of the power reservoir and the retaining member is released during dose dispensing.

An example of a power reservoir suitable for the present disclosure is a compression spring, preferably a pre-strained pressure spring. The use of a spring or the like has the benefit that the user force required to expel the contents of the cartridge. A pre-strained spring has the further advantage to reduce the force required during dose setting. As an alternative to a pre-strained spring, a spring or other suitable power reservoir may be used which is charged or strained during dose setting. Another benefit of devices where the force required to expel the contents of the cartridge is provided by a power reservoir instead of the user is that a dial extension of the device may be avoided, which means that the size of the device remains the same irrespective of whether a dose is set or the amount of the set dose. This makes the device more compact and user-friendly.

The retaining member is preferably a flexible element with high tensile modulus and strength, like glass or aramid fibre reinforced poly-urethane. The retaining member may have the form of a belt or cable. As the load acting on the retaining member is a tensile force, the drive mechanism may be further reduced in size by winding the retaining member on a spool or the like which is not possible with pressure loaded piston rods. In addition, the retaining member may be compact in size compared to a piston rod which requires a compressive stiffness for transmitting axial pressure loads.

The plunger may be constrained to one end of the retaining member. Preferably, it is axially, i.e. in the longitudinal direction of cartridge, fixed to the retaining member. As an alternative, the plunger may be a unitary part of the retaining member, for example a widened end thereof.

According to a preferred embodiment, the release member is in its second state rotatable relative to the housing. For example, the retaining member is attached to and wound on a drum or spool which is in gear engagement with the release member. Thus, rotation of the release member allows the retaining member to unwind from the drum or spool a desired distance corresponding to the distance the plunger is pushed into the cartridge under the action of the spring or the like. As an alternative, the retaining member may be directly attached to and wound on the release member. Winding the retaining member of the plunger onto the drum and/or the release member generates a torque in these component parts as the spring acts on the plunger. This torque is measured during assembly to avoid the requirement of a priming step performed by the user of the device.

The dose setting member is preferably rotatable relative to the release member during dose setting and rotates together with the release member during dose dispensing. Preferably, the dose setting member and the release member are arranged rotatable within the housing with their respective axis of rotation being perpendicular to the longitudinal axis of the housing. This arrangement of the component parts has advantages regarding size and ease of use of the device.

The dose setting member and the release member may be arranged coaxially. This common axis may however be offset from the axis of a drum or spool to which the retaining member may be attached.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring force needed for dispensing very high doses, while still being suitable for a wide range of patients needing different dose sizes. Preferably, the limits for the minimum dose and the maximum dose are provided by hard stop features. For example, the rotation of the dose setting member relative to the housing is limited by rotational stops defining a minimum dose position and a maximum dose position. The minimum dose stop has to be robust enough to withstand the load exerted by the power reservoir via the retaining member.

The drug delivery device may further comprise a trigger which is axially movable in the direction of the axis of rotation of the dose setting member. Actuation of the trigger switches the release member between its first and second state. For example, the trigger may act on a clutch which constrains the release member to the housing in its first state, i.e. when the trigger is not actuated, and which allows rotation of the release member for dose dispensing as soon as the trigger is actuated.

According to a further embodiment of the present disclosure a dispensing speed control mechanism is provided for use in an injection device having a release button or trigger, which is displaceable to initiate dispensing of a set dose, a first component part, which is driven by a power reservoir during dose dispensing, and a second component part, which is stationary during dose dispensing. The speed control mechanism comprises friction means for decelerating the first component part during dose dispensing depending on the position of the release button. In other words, the user is able to control the dispensing speed by increasing or decreasing friction within the device and thus use either the full dispensing speed provided by the power reservoir or a speed reduced due to the internal friction.

Preferably, the release button or trigger has to be depressed a first distance to initiate dose dispensing, e.g. by releasing a clutch, and may then be depressed further a second distance to control and amend dispensing speed. This may include examples where due to the position of the release button there is either friction decelerating the driver or not. As an alternative, the magnitude of the friction decelerating the driver may be individually and preferably steplessly amended or adjusted by varying the position of the release button or trigger.

In a preferred embodiment, the friction is at a high level just after the button or trigger is depressed the first distance and decreases as the button or trigger is pressed further for the full or fractions of the second distance. Typically, the release button or trigger is pressed in an axial direction of the housing and relative to the housing.

The dial gear may be provided in the drug delivery device which is rotationally coupled to the release member during dose dispensing. Thus, decelerating the dial gear may be used to control dispensing speed. In general, there are different ways to create the friction decelerating a dial gear or the like component of the device. For example, a component part may be pressed against for the dial gear. As an alternative, a ratchet may be provided which may be brought into and out of engagement with the dial gear. Further, a flexible element may be used which acts on the dial gear. According to a preferred embodiment the friction means comprises a multi-plate clutch system acting between a stationary component part and the (rotating) dial gear. The multi-plate clutch system may comprise a spring, at least one first clutch plate, which is rotationally constrained to the dial gear, and at least one second clutch plate, which is rotationally constrained to the housing at least during dose dispensing. The spring may press the clutch plates against each other, thus creating friction between a rotating and a non-rotating plate, which thus decelerates the dial gear.

Preferably, the multi-plate clutch system further comprises a cage which is rotationally constrained to the housing at least during dose dispensing and which is rotationally constrained to the second clutch plate(s), wherein the spring biases the cage towards at least one component part of the dial gear. Amending the axial position of the spring, the cage and/or the dial gear results in a variation of the friction decelerating the dial gear during dose dispensing.

According to a further embodiment of the present disclosure the handheld injection device comprises clicker components. Different clicker mechanisms may be active during dose setting and dose dispensing. For example, a dose setting feedback may be generated between the housing and a dial member. A dose dispensing feedback may be generated between a chassis fixed to the housing and the release member. To provide an additional non-visual, i.e. an audible and/or tactile, feedback to a user only at the end of dispensing of a set dose, a clicker between the chassis and the dial gear may be active as the device returns to its minimum dose stop. To differentiate between these feedback signals, the end of dose dispensing feedback, which is generated only at the end of dispensing of a set dose, is distinct from the further feedback(s). For example, a different sound may be generated.

In addition to the non-visual feedbacks, drug delivery devices usually have a display indicating the actually set dose. For example, a number wheel may be arranged coaxially with and rotationally coupled to the dose setting member with a series of markings being provided on the outer circumference of the number wheel.

Preferably, the drug delivery device further comprises a prism arranged relative to the number wheel such that the series of markings on the number wheel is visible in the direction of the axis of rotation of the dose setting member. The use of a simple prism requires that the markings on the number wheel are arranged reversed (mirrored) to be readable through the prism. As an alternative, a penta-prism may be used instead of a simple prism. The surface of the prism may be designed to provide a magnification of the markings on the number wheel. As an alternative to the use of a prism, the housing may have a lateral opening or window through which the markings on the number wheel are visible.

The drug delivery device may comprise a dose dial grip for dose setting and clutch means (which may comprise one or more clutches) coupling the dose dial grip rotationally to the dose setting member during dose setting and rotationally de-coupling the dose dial grip from the dose setting member and coupling the dose setting member rotationally to the release member during dose dispensing. Preferably, this clutch is actuated by the trigger. This arrangement of the clutch has the benefit that the dose dial grip is free to spin during dose dispensing without interfering with the components moving during dispensing. As an alternative, the dose dial grip may be constrained to the housing during dispensing.

According to a further aspect of the present disclosure, the drug delivery device further comprises a nut which is guided axially displaceable and non-rotatable with respect to one of the dose setting member and the release member. For example, the nut and the dose setting member or the release member are provided with corresponding splines and notches. The nut further has a thread engaging a thread of the other of the dose setting member and the release member such that relative rotation between the dose setting member and the release member during dose setting causes the nut to move towards an end stop. According to the present disclosure an injection device may comprise a cartridge containing a medicament and a drive mechanism as mentioned above. The nut and the end stop may be provided in the drive mechanism of the injection device such that the nut prevents setting of a dose exceeding the (dispensable) amount of a medicament in the injection device. In other words, the end stop preferably defines the length of a track on which the nut travels during dose setting, wherein the length of the track corresponds to the total (dispensable) amount of medicament in the cartridge.

The device according to the present disclosure is preferably a disposable injection device. It has low torque requirements to set a dose, low force requirements to trigger dispense of medicament and permits any dose to be selected within a range of zero to a pre-defined maximum. It has relatively low part count, very compact size and is particularly attractive for cost sensitive device applications.

The term ["medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

The present disclosure will now be described in further detail with reference to the accompanying schematic drawings, wherein.

DETAILED DESCRIPTION

Figure 1:
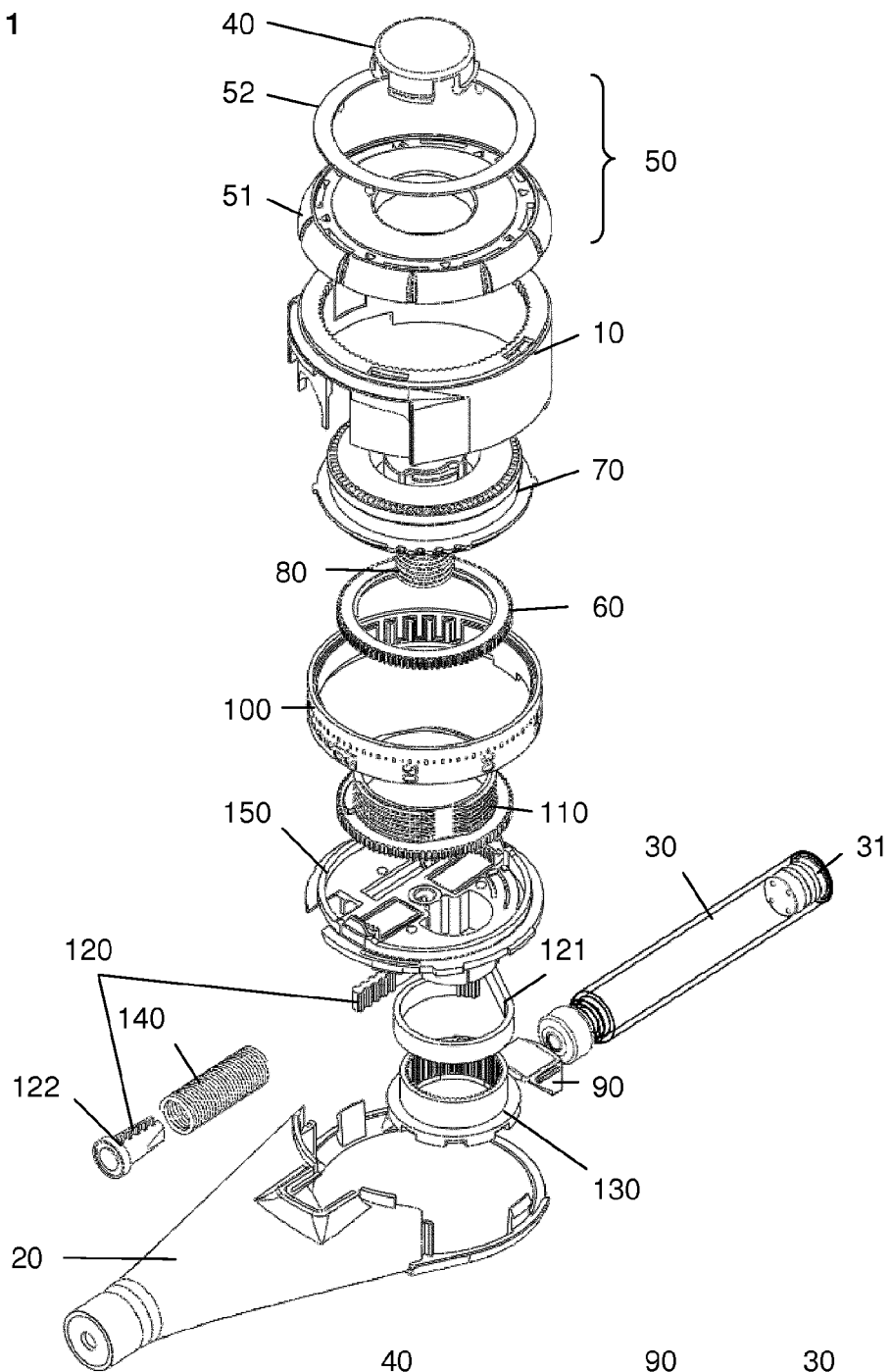
FIG. 1 shows an exploded view of an injection device comprising a drive mechanism.
Figure 2:
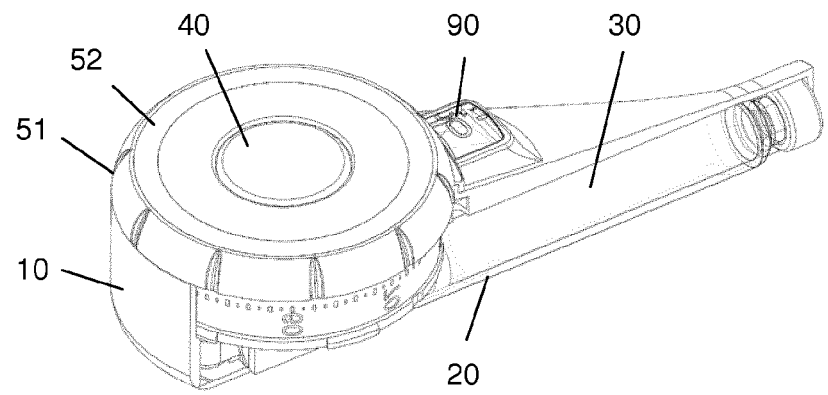
FIG. 2 shows a perspective view of the device of FIG. 1.

FIGS. 1 and 2 show views of the drug delivery device. FIG. 1 illustrates the component parts incorporated into the injection device which are a body 10, a cartridge holder 20, a trigger 40, a dial member 50 comprising a dial 51 and a dial cover 52 a medicament cartridge 30, a last dose nut 60, a dial gear 70, a trigger spring 80, a prism 90, a number wheel 100, a release gear 110, a belt assembly 120, a belt gear 130, a main spring 140 and a chassis 150.

The body 10, the cartridge holder 20 and chassis 150 form a housing which has a distal end at the side receiving the cartridge 30 (right hand side in FIG. 2) and an opposite proximal end. The cartridge holder defines a longitudinal axis of the housing. A rotational axis is provided perpendicular to this longitudinal axis with the trigger 40, the dial member 50, the last dose nut 60, the dial gear 70, the trigger spring 80, the number wheel 100 and the release gear 110 are arranged concentrically about this rotational axis. The cartridge holder 20 may comprise a cartridge retaining part and a separate rear part (not shown).

The medicament cartridge 30 is housed within the cartridge holder 20. The cartridge holder 20 is rigidly constrained in the body 10. The cartridge holder 20 provides location and containment of the medicament cartridge and prism 90.

Figure 3:
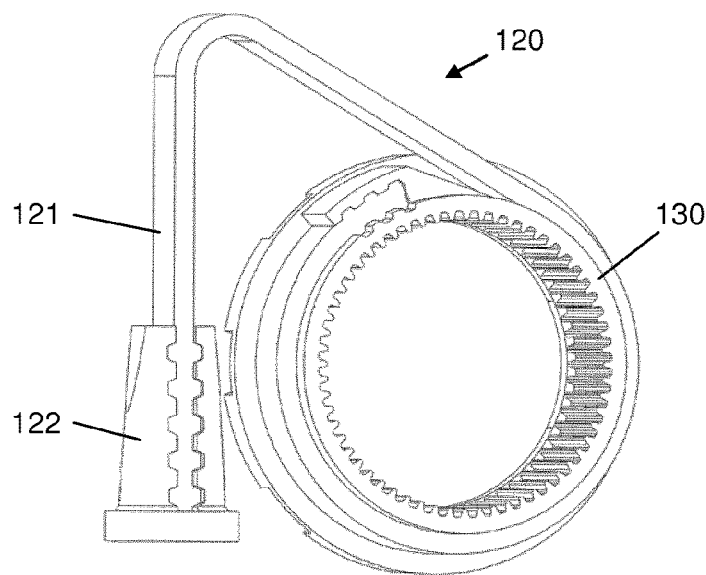
FIG. 3 shows a top view of components of the drive mechanism of FIG. 1.

The belt assembly 120 comprises a belt 121 and a plunger 122. The belt 121 is a flexible element with high tensile modulus and strength. Suitable materials include glass or aramid fibre reinforced poly-urethane. Features at each end of the belt 121 provide axial constraint and allow it to carry a tensile load. The distal end of the belt 121 is connected to the plunger 122 via spline features as shown in FIG. 3. The opposite end of the belt 121 is restrained by the belt gear 130 and partially wound onto it. FIG. 3 shows the belt 121 assembled to the belt gear 130 in the "as delivered" condition (prior to any doses being delivered).

Figure 4:
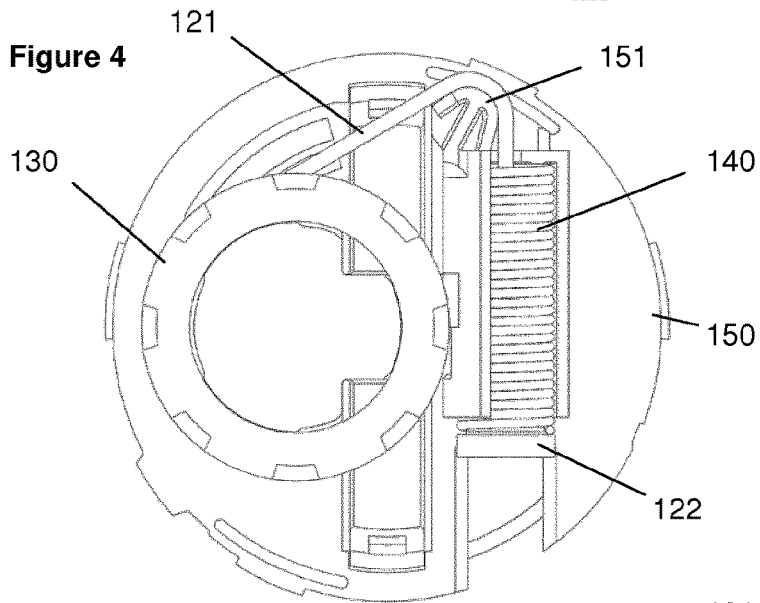
FIG. 4 shows a bottom view of components of the drive mechanism of FIG. 1.

The distal face of the plunger 122 abuts a bung of the medicament cartridge 30 and the main spring 140 acts directly on the proximal surface of the plunger 122. It is the main spring 140 acting on the plunger 122 that drives the bung axially in order to deliver medicament. Tension in the belt 121 prevents the main spring 140 releasing and, therefore, by controlling the release of the belt 121, accurate control of the medicament delivery can be achieved. FIG. 4 shows the main spring 140 in its fully compressed state, i.e. the state prior to dispensing the first dose, interposed between the plunger 122 and a bearing face of the chassis 150. The belt 121 is held in tension by the main spring 140 and follows a curved path in the device defined by a belt guide feature 151 on the chassis 150.

The main spring 140 is supplied to the user in the fully charged state (near "coil bound"). It acts between the proximal face of the plunger 122 and an abutment on the chassis 150. Tension in the belt 121 prevents the energy stored in the main spring 140 from being released until a dose is dispensed.

Figure 5:
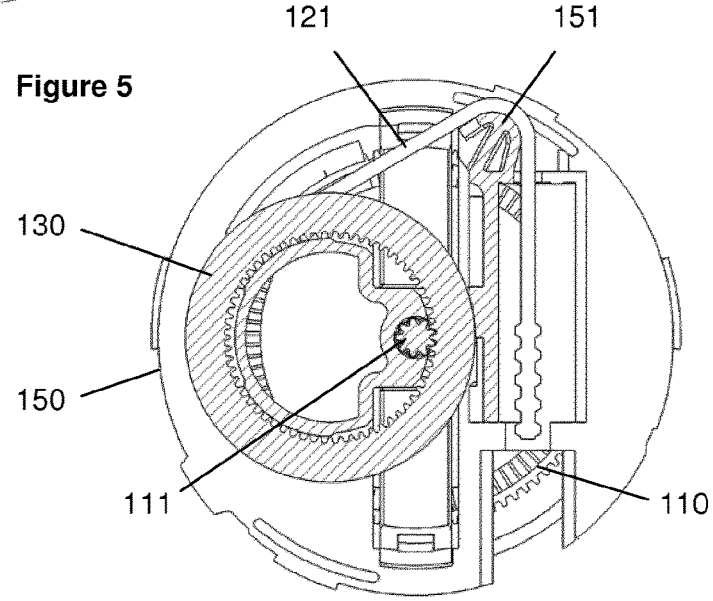
FIG. 5 shows a perspective view of components of the drive mechanism of FIG. 1, FIGS. 6a, 6b show sectional views of components of the device of FIG. 1, FIGS. 7a, 7b show details of the device of FIG. 1 in the minimum dose position and in the maximum dose position.

The belt gear 130 controls release of the belt 121 through a geared interface with a pinion 111 of the release gear 110. It is radially constrained by the chassis 150 via a combination of abutments. The combined effect of these abutments ensure that the resultant force acting on the belt gear 130 from the belt 121 biases the geared interface with pinion 111 of the release gear 110 into engagement as shown in FIG. 5. This acts to minimize backlash between the gears and also reduce the risk of disengagement in the event of shock loading.

Figure 6A:
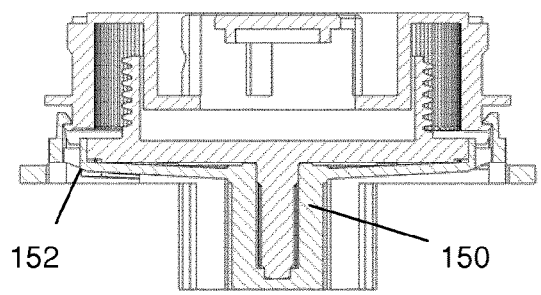
Figure 6B:
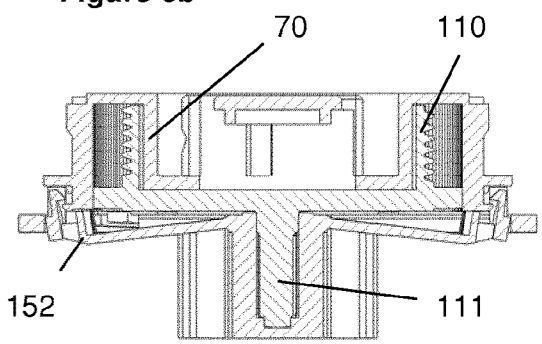

The chassis 150 locates the mechanism within the body 10 and is rigidly fixed into the body 10 via spline and spring clip features. It provides location for the belt gear 130 and belt 121. Flexible features within the chassis 150 (chassis locking arms 152) fix the release gear 110 rotationally during dialing (FIG. 6a) but disengage to allow rotation during triggering (FIG. 6b). Abutments adjacent to these chassis locking arms 152 provide tangential support and prevent excessive deflection when loaded by the release gear 110.

Figure 7A:
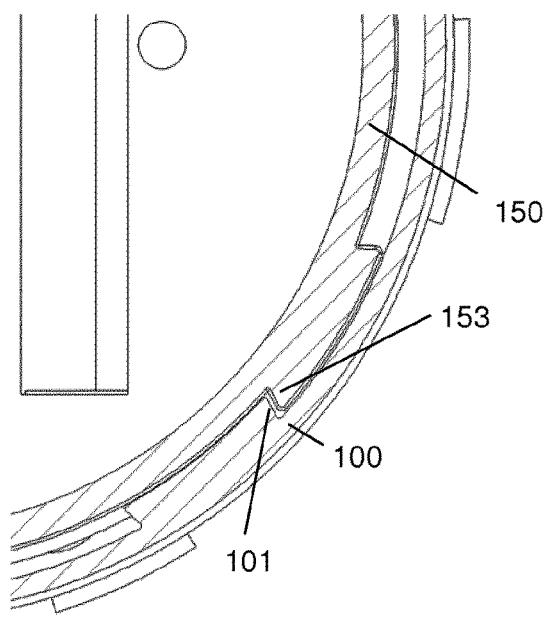
Figure 7B:
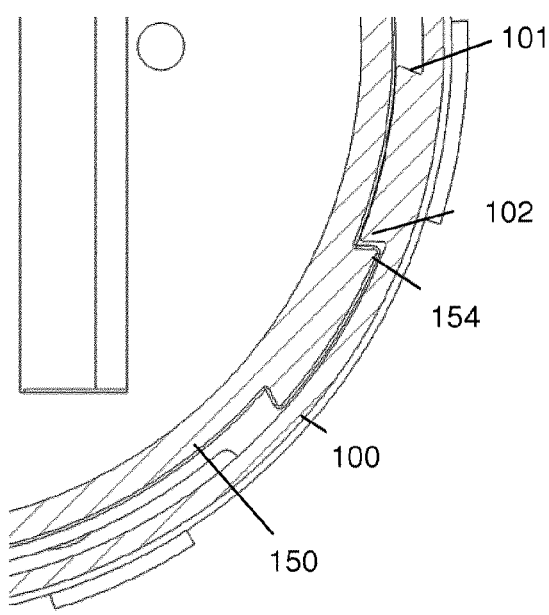
Figure 8:
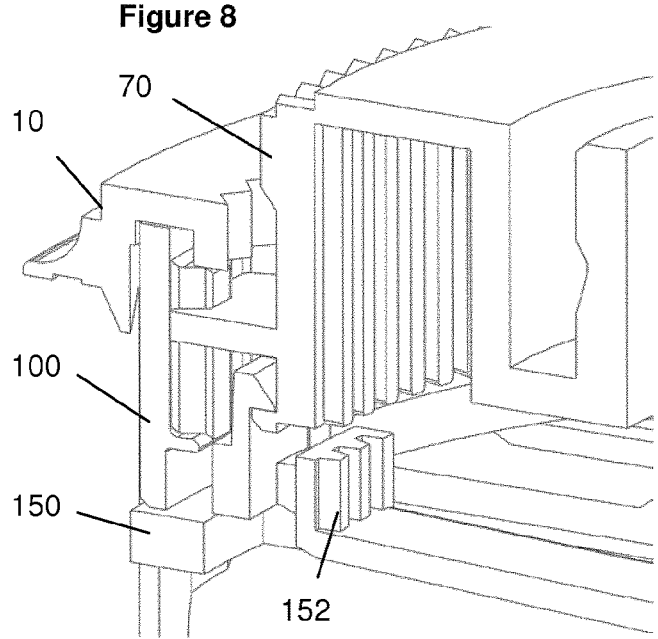
FIG. 8 shows a detail of the device of FIG. 1.

The number wheel 100 incorporates stop features 101, 102 which engage with abutments 153, 154 on the chassis 150 and correspond with the minimum (FIG. 7a) and maximum (FIG. 7b) dose set. This restricts the maximum dose that may be set and creates the end of dose stop when the mechanism returns to the zero unit position. The number wheel 100 is printed with a series of numbers on the external surface which create the dose display when viewed through the prism 90. The number wheel 100 is rotationally coupled to the dial gear 70 as shown in FIG. 8. Further, the number wheel is axially located between the chassis 150 and the body 10 and radially constrained by the body 10.

Figure 10:
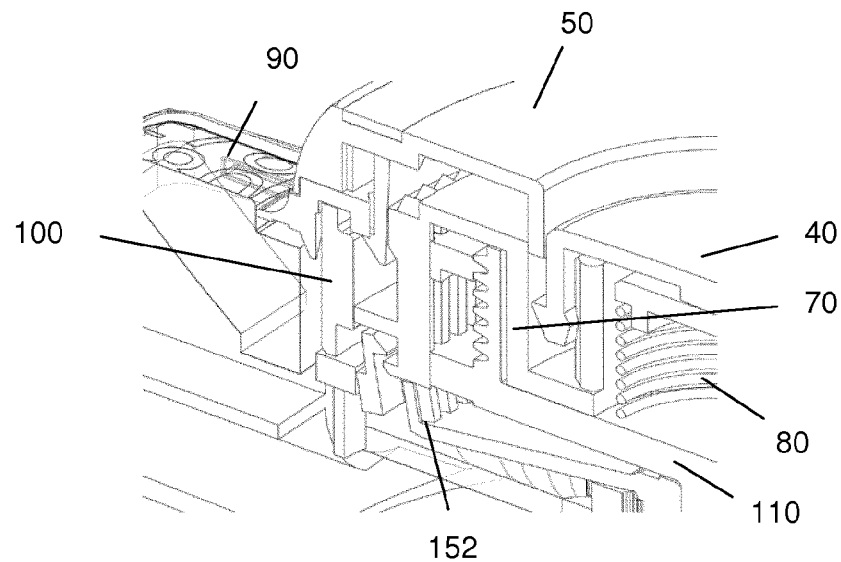
FIG. 10 shows a detail of the device of FIG. 1 in the dose dispensing condition.

The dose set is displayed on the outer surface of the device to provide feedback to the user. In this embodiment, the prism 90 reflects the display from the number wheel 100 so that the dose is displayed on the front face of the device (upper side in FIG. 2). The prism 90 is retained within the cartridge holder 20 and body 10 once assembled as shown in FIG. 10. The prism 90 uses the phenomenon of "Total Internal Reflection" to achieve reflection of the number without any special treatment to the surfaces (such as metal coating). The nature of this prism is that the display is mirrored. To account for this, the printing on the number wheel 100 is reversed so the net effect provides a conventional dose number display. An additional function of the prism 90 is that the surfaces can be designed to also provide magnification, in addition to the primary function of reflection.

Alternative prism arrangements (for example a pentaprism) could perform the same function without mirroring the display if required. An alternative embodiment negates the requirement for the prism 90 component and displays the dose on the side of the device. The number wheel 100 is then printed with conventional, non-mirrored, text and a small window is formed in the side of the body 10.

Figure 9:
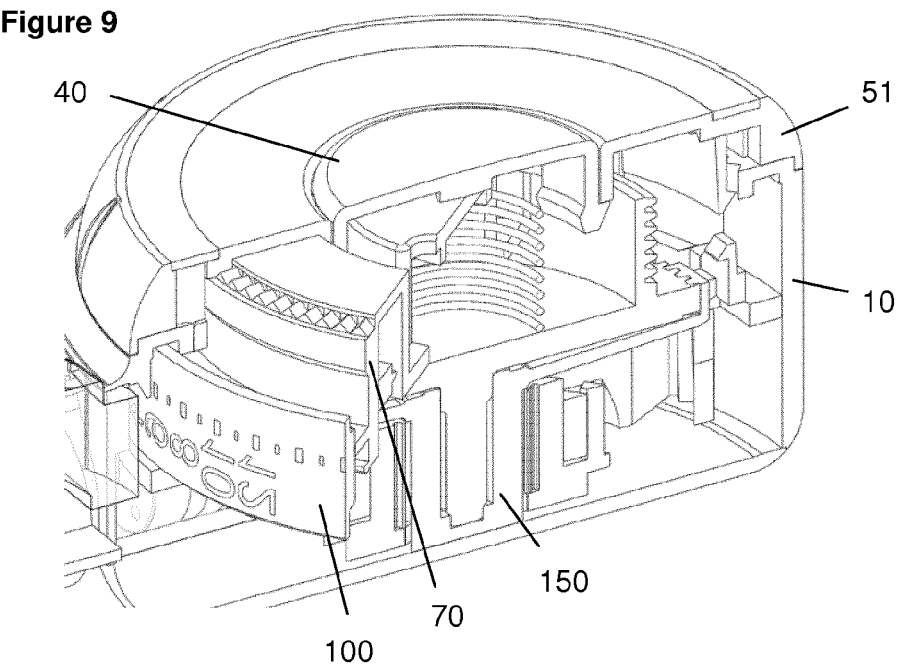
FIG. 9 shows a detail of the device of FIG. 1 in the dose setting condition.

The dial gear 70 is rotationally coupled to the dial member 50 during dialing (FIG. 9) and rotationally coupled to the release gear 110 during dispense (FIG. 10). The dial gear 70 may translate axially between abutments provided by the release gear 110 and the dial member 50 and is biased into contact with the dial member 50 via the trigger spring 80 when the trigger 40 is not depressed. The trigger spring 80 acts between the dial gear 70 and release gear 110. The chassis locking arms 152 are axially coupled to the dial gear 70 with snap clips which permit relative rotation.

Figure 11:
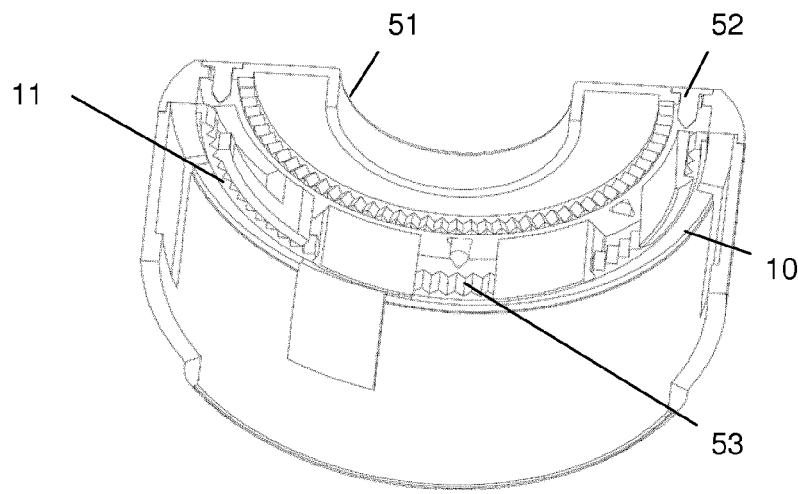
FIG. 11 shows a detail of the device of FIG. 1.

The dial member 50 comprises the dial 51 and the dial cover 52 which are permanently and rigidly fixed together. The dial member 50 is axially and radially located in the body 10 via snap clips and the rotational position is detented via a flexible cantilever arm 53 locating in radial ratchet teeth 11 within the body 10 (FIG. 11). These detent features provide positive feedback to the user during dialing and align the dial member 50 and number wheel 100 with the body 10 so the units of the dose display accurately align with the prism 90.

Figure 12:
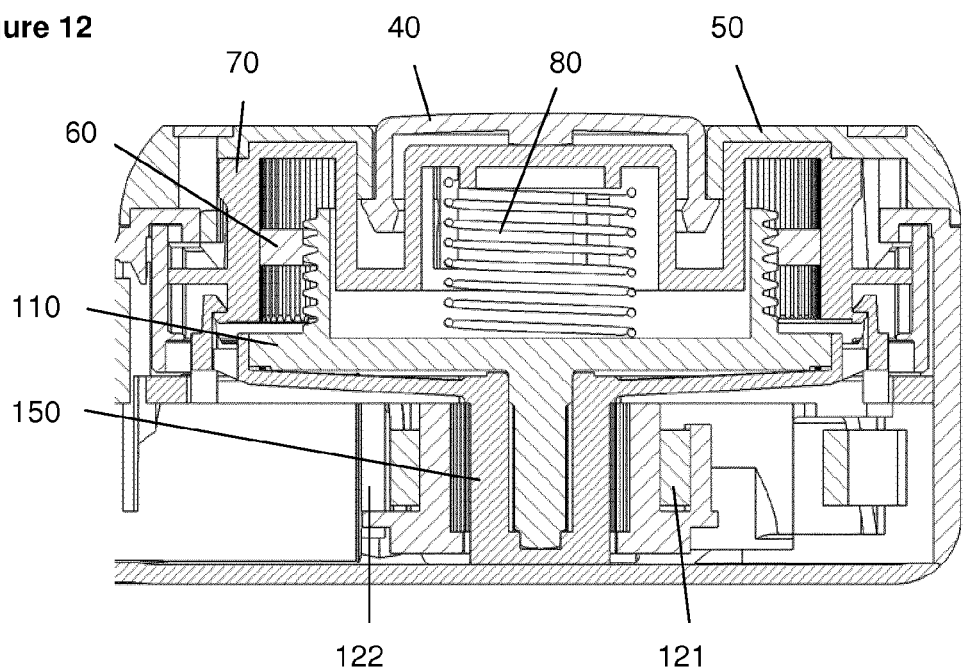
FIG. 12 shows a sectional view of a detail of the device of FIG. 1.

The trigger 40 is snap fitted into the dial member 50 and axially constrained between abutments on the dial member 50 and dial gear 70. The user may axially translate the trigger 40 between these abutments by overcoming the force of the trigger spring 80 which is transferred through the dial gear 70 (FIG. 12).

During dose setting, the release gear 110 is in toothed engagement with the belt gear 130 and rotationally fixed by the chassis locking arms 152. When the trigger 40 is depressed, the release gear 110 is rotationally coupled to the dial gear 70 and is released from the chassis locking arms 152. It is axially constrained between the dial gear 70 and chassis 150 and is biased toward the chassis 150 abutment by the trigger spring 80.

The mechanism incorporates a last dose nut 60 to prevent setting of a dose greater than that which remains within the medicament cartridge. This is positioned between the dial gear 70 and release gear 110 since the dial gear 70 rotates relative to the release gear 110 during dose set and not during dispense. The last dose nut 60 is splined to the inner surface of the dial gear 70 and threaded to the release gear 110 such that clockwise rotation of the dial member 50 rotates the last dose nut 60 and translates it towards the last dose stop on the release gear 110.

Figure 13:
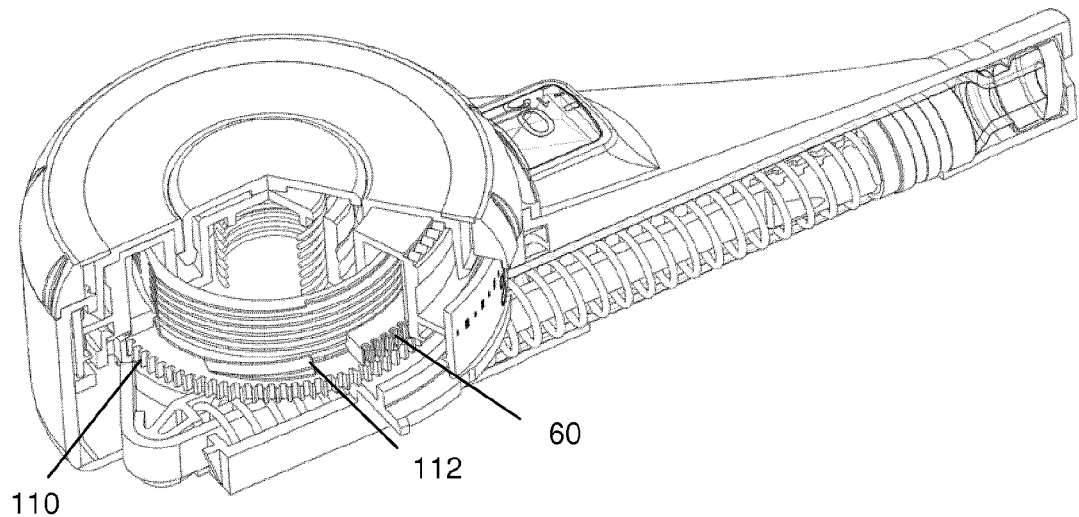
FIG. 13 shows the device of FIG. 1 with an empty cartridge.
Figure 14:
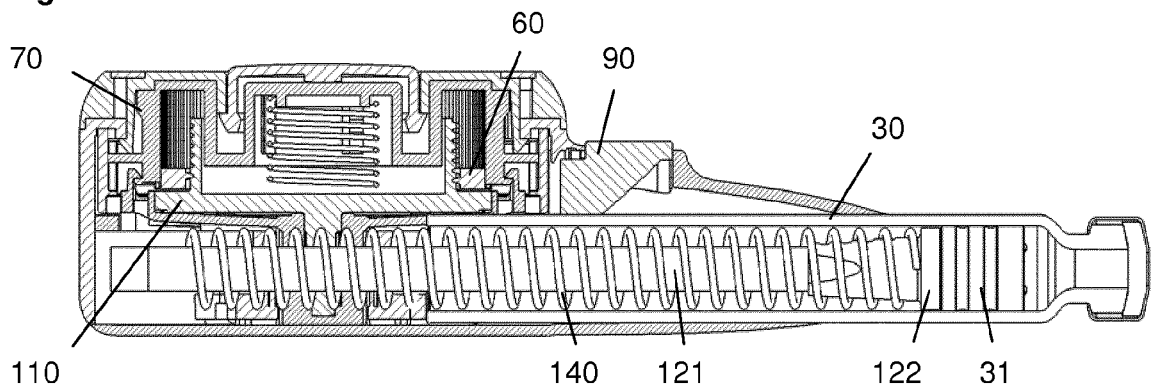
FIG. 14 shows the device of FIG. 1 with an empty cartridge.

The last dose nut 60 is successively translated towards the stop as doses are set until the cartridge dose limit is reached. At this point the last dose nut 60 contacts the abutment 112 on the release gear 110 which prevents further clockwise rotation of the last dose nut 60 and, therefore, rotation of the dial gear 70 and dial member 50. FIGS. 13 and 14 show the device shortly before the nut contacts abutment 112. The number of permissible rotations of the last dose nut 60 is determined by the capacity of the cartridge 30.

Figure 15:
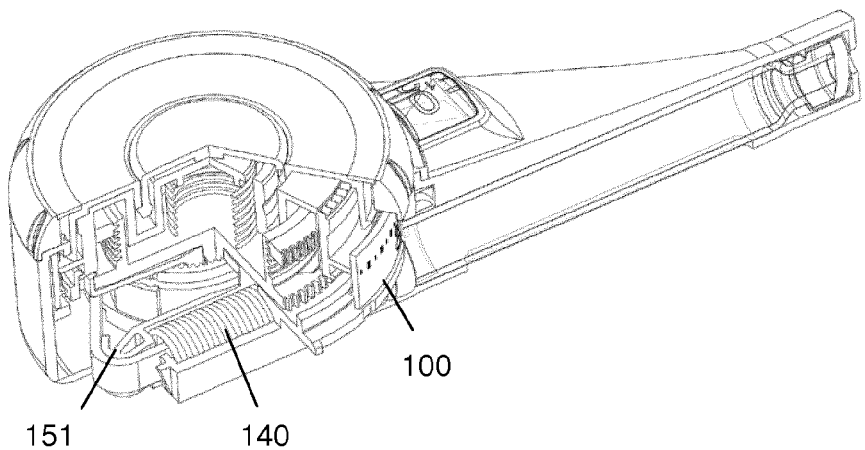
FIG. 15 shows the device of FIG. 1 with a full cartridge prior to dose setting.
Figure 16:
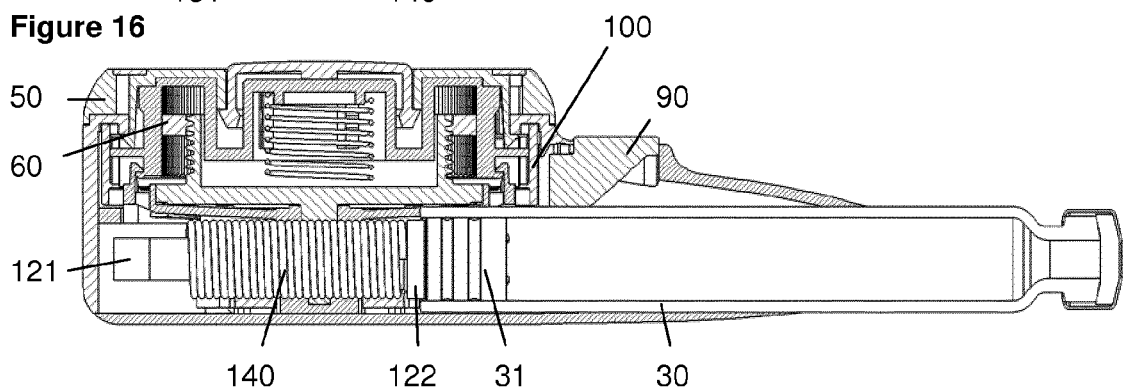
FIG. 16 shows the device of FIG. 1 with a full cartridge prior to dose setting.

The dial member 50 is rotated by the user in a clockwise direction to set a dose starting from the position shown in FIGS. 15 and 16. The dose can be cancelled by rotating the dial member 50 in a counter-clockwise direction either before any dispense or, alternatively, if the trigger 40 is released mid-dispense, the remaining dose may be cancelled.

Figure 17:
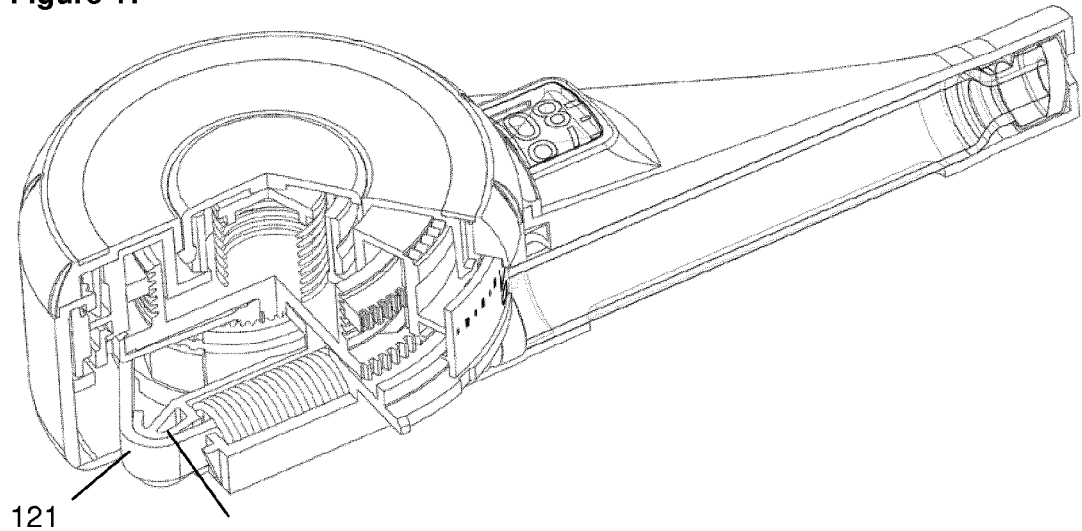
FIG. 17 shows the device of FIG. 1 with a full cartridge with maximum dose set.
Figure 18:
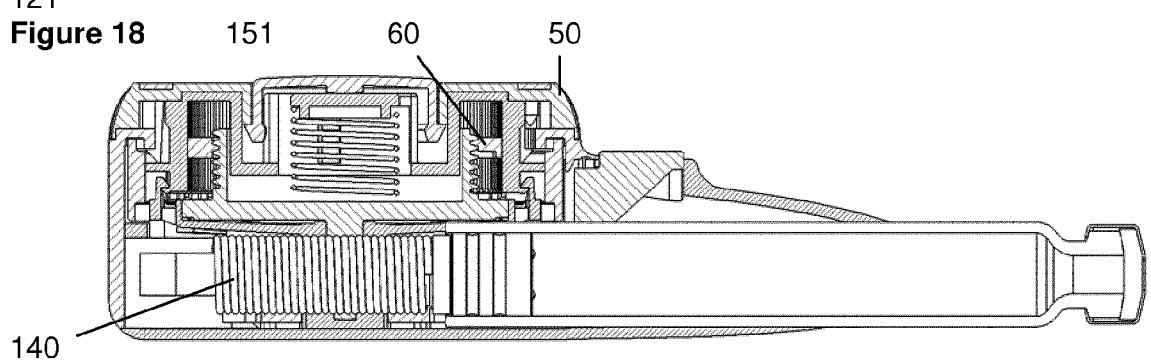
FIG. 18 shows the device of FIG. 1 with a full cartridge with maximum dose set.

The selected dose is displayed through the body 10 via the number wheel 100 and prism 90 as described previously. Irrespective of whether the dial member 50 is rotated clockwise or counter-clockwise the dose displayed will always indicate the dose to be dispensed. In addition, the dose display also decrements as the dose is dispensed and thus displays the dose remaining to be dispensed. As the dose is dialed up the number wheel 100 is driven away from the zero unit stop 153 on the chassis 150 and towards the maximum unit stop 154. The dial member 50 can be rotated by the user in both clockwise and counter-clockwise directions when the number wheel 100 is not in contact with the zero dose stop abutment 153 or maximum dose stop abutment 154 of the chassis 150. The zero unit abutment 153 prevents counter-clockwise rotation of the dial member 50 below the zero unit position. The maximum dose abutment 154 prevents setting of a dose greater than the mechanism maximum which is depicted in FIGS. 17 and 18.

The detent features 11, 53 between dial member 50 and body 10 controls the position of the dial member 50 to ensure that discrete units are selected and that the spline features between dial member 50 and release gear 110 are correctly aligned to permit spline meshing when the device is triggered.

During dose setting, the release gear 110 is biased by the trigger spring 80 into engagement with the locking arms 152, which then couple the release gear 110 to the chassis 150. The release gear 110 is therefore fixed rotationally during dose set. This in turn prevents rotation of the belt gear 130 and, therefore, release of the belt 121.

Figure 19A:
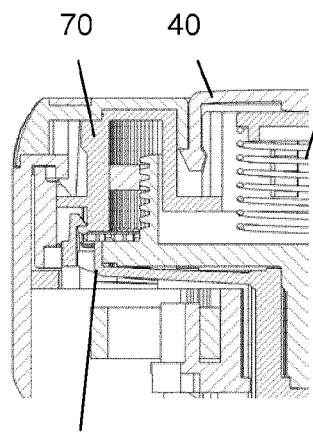
FIGS. 19a to 19c show a trigger actuation sequence of the device of FIG. 1, FIGS. 20a, 20b show details of the device of FIG. 1, FIGS. 21a to 21c show an end of dose click sequence of the device of FIG. 1, FIGS. 22a to 22c sectional views of a detail of a drug delivery device according to a second embodiment.
Figure 19B:
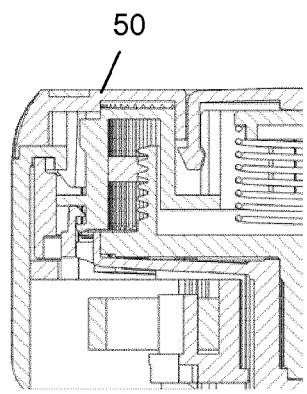
Figure 19C:
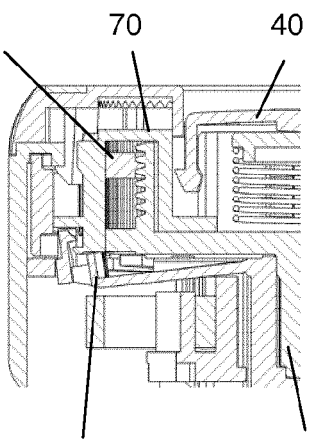

The device may be triggered by the user through application of an axial force on the trigger 40 (FIG. 19a). The trigger 40 acts on the dial gear 70, translating the dial gear 70 and chassis locking arms 152, compressing the trigger spring 80. As the dial gear 70 translates it first decouples from the dial member 50 as the face teeth disengage. At this stage (mid trigger position, FIG. 19b) the dial member 50 can no longer be rotated in either direction since the dial member 50 detent arm 53 is prevented from deflecting by an annular abutment on the dial gear 70. Further translation of the trigger 40 couples the dial gear 70 to release gear 110 via splines and finally decouples the release gear 110 from the chassis 150 (FIG. 19c).

On triggering, the release gear 110 rotates, controlled by the dial gear 70 and number wheel 100. The belt gear 130 rotates, due to the torque generated by the main spring 140 acting through the belt 121. As the main spring 140 extends, the plunger 122 is driven against the bung, creating a distal translation and causing medicament to be dispensed. Since the release gear 110, dial gear 70 and number wheel 100 are rotationally coupled, the number wheel 100 also rotates during dispense in a counter-clockwise direction, returning towards the zero unit stop 101, 153. At the zero unit position the number wheel 100 contacts the abutment 153 on the chassis 150, preventing further rotation of the dial gear 70, release gear 110 and belt gear 130, stopping release of the belt 121 and any further dispense of medicament.

The trigger 40 is subsequently released, re-engaging the chassis locking arms 152 to lock the rotational position of the release gear 110, belt gear 130, belt 121, plunger 122 and main spring 140 independently from the zero unit stop between chassis 150 and number wheel 100. This allows the next dose to be set without immediate release of the main spring 140. Aside from the last dose nut 60, release gear 110, belt gear 130, belt 121, plunger 122 and main spring 140 all other components in the device return to their original positions once the entire dose has completed dispense.

Figure 20A:
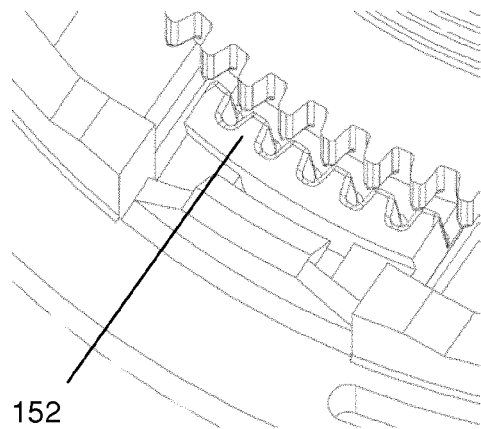
Figure 20B:
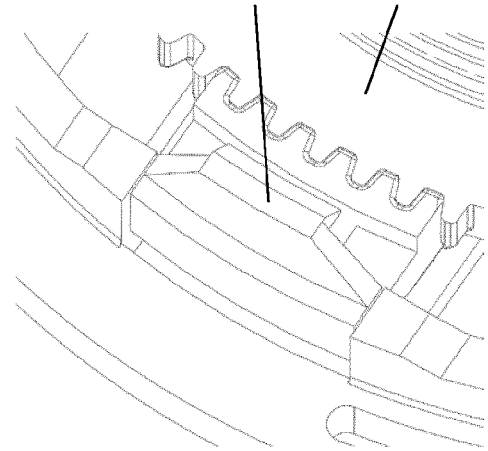

The release gear 110 splines that engage with the chassis locking arms 152 are angled so the release gear 110 is turned against the torque induced by the main spring 140 as they re-engage when the trigger 40 is released (FIGS. 20a, 20b). Back-winding the release gear 110 ensures that the chassis locking arms 152 react the main spring 140 force in place of the zero unit stop as the trigger 40 is released. This prevents the release gear 110 rotating to take up clearance at this interface when the subsequent dose is dialed (and the zero unit stop is disengaged), which could lead to the dispense of some fluid.

Feedback is provided to the user during dose setting by the interaction between the dial member 50 detent arm 53 and the body 10 ratchet features 11. Dispense feedback is created through interaction between the chassis 150 and ratchet features on the release gear 110. A cantilever arm on the chassis 150 rides over the ratchet features on the release gear 110.

A single, distinctive click is created as the device returns to the zero unit stop. This provides clear feedback to the user that the dose has been completed in addition to the dispense clicker ceasing. A cantilever arm 155 in the chassis 150 engages with the dial gear 70 when in the dispense condition. This arm is deflected as the dial gear 70 approaches the zero unit stop and rapidly released as the dial gear 70 engages the zero unit stop (FIGS. 21a to 21c).

It is possible to incorporate a mechanism that allows the user to control the speed of dispense by the distance that they move the trigger 40. In this second embodiment the features and functions are identical to the first embodiment as described above. However, an additional system 160 is included as shown in FIGS. 22a to 22c.

The embodiment shows a multiplate clutch system 160 integrated into the device acting between the dial member 50 (which is locked during dispense) and dial gear 70. The system comprises a carrier 161 which is splined to the dial member 50, a clutch spring 162 and a clutch pack comprising rotating plates 163 which are splined to the dial gear 70 and static plates 164 which are splined to the dial member 50 via carrier 161.

Figure 22C:
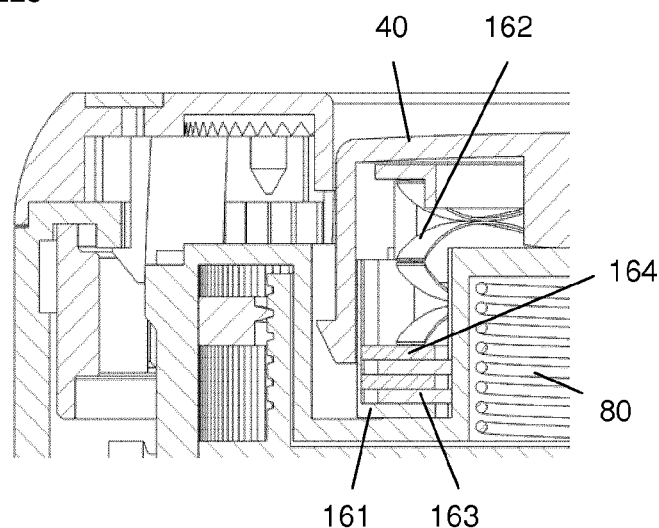
Figure 23:
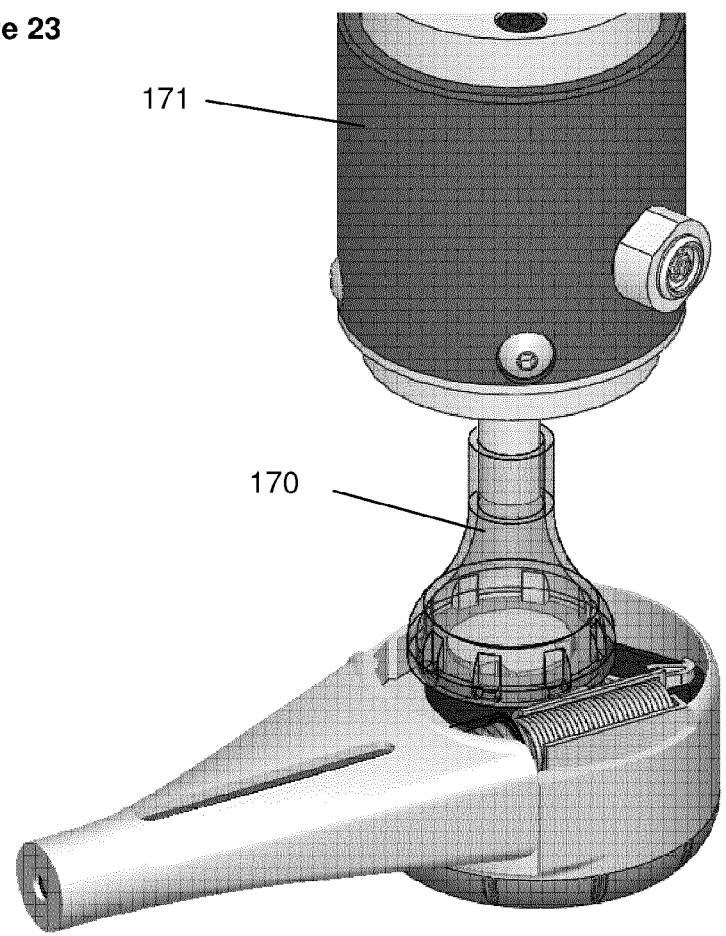
FIG. 23 shows the device during assembly.

For the embodiment shown in FIGS. 22a to 22c, force applied to the clutch pack 163, 164 from the clutch spring 162 reduces as the trigger 40 is depressed. Multiple clutch plates 163, 164 increase the torque capacity of the clutch for a given clutch spring force. In this embodiment, the overall trigger 40 travel is increased to 4.5 mm, 2.25 mm for mechanism disengagement and 2.25 mm for user variable speed control.

The facility for removing the need for a user to prime the device when first used can also be incorporated. This involves removing the variable distance (dependent on component and cartridge tolerances) between the cartridge bung 31 and the plunger 122 during manufacture such that the plunger 122 is in contact (and applies a small force) to the bung when assembled. This "prime elimination" is achieved using the following method: The cartridge holder 20 is preferably divided into two separate components (cartridge retainer and rear part) and the device is assembled omitting the rear part. Alternatively, a suitable opening is provided in the device which may be closed after the priming operation. A small dose of approximately 10 units is dialed by rotating the dial member 50 as the user would. The belt gear 130 is rotationally coupled to an assembly tool 170 with torque measurement capability (torque sensor 171). The trigger 40 is depressed to release the mechanism and the torque generated in the belt gear 130 is measured as it is rotated clockwise via the assembly tool 170, thus releasing belt 121 length. As the belt 121 is released, the plunger 122 approaches the bung 31 under the main spring 140 force. When the plunger 122 contacts the bung 31, the bung will begin to react a proportion of the main spring 140 force, thus reducing the belt gear 130 torque. Measurement of this change in torque as the belt 121 is released allows a specific force to be applied to the bung 31 by the main spring 140. Release of the trigger 40 subsequently locks the mechanism and any set doses remaining are then dialed to zero. Finally, the rear part of cartridge holder 20 is clipped into position to complete the assembly.

The invention claimed is:

1. A method comprising:
providing a cartridge with a bung, a plunger, a spring biasing the plunger towards the bung, and a release member coupled to the spring such that release of the spring is controlled by the release member;
providing a housing and a dose setting and dispensing mechanism, the dose setting and dispensing mechanism comprising a dose setting member, a trigger, the release member and/or a drum, the plunger, and the spring, and the spring being a strained pressure spring;
mounting the cartridge with the bung, the dose setting and dispensing mechanism, the plunger, and the spring within the housing such that the spring biases the plunger in a dispensing direction and such that the drum and/or the release member is attached to the plunger;
providing a tool comprising a sensor for measuring a torque or force of the spring;
attaching the tool to the drum and/or the release member of the dose setting and dispensing mechanism in a state in which the drum and/or the release member is accessible from outside the housing;
rotating the dose setting member in a first direction to set a dose and activating the trigger to release the spring while monitoring the torque or force measured by the sensor;
releasing the trigger and stopping the release member upon detection of a predetermined change in the torque or force measured by the sensor, wherein the predetermined change in the torque or force is a rapid decrease in the torque or force due to the plunger contacting the bung in the cartridge; and releasing the tool from the drum or the release member.

2. The method according to claim 1, wherein after the trigger is released, rotating the dose setting member in a second direction opposite to the first direction.

3. The method according to claim 1, wherein if the predetermined change in the torque or force is not detected, releasing the trigger after the plunger moves in the dispensing direction a distance corresponding to the dose set by rotating the dose setting member and thereafter rotating the dose setting member, the activating the trigger, and monitoring the torque or force are repeated.

4. The method of claim 1, wherein rotating the dose setting member and activating the trigger while monitoring the torque or force measured by the sensor comprises releasing a retaining member coupled to the plunger such that the spring moves the plunger in the dispensing direction.

5. The method of claim 4, wherein the retaining member is a belt, and releasing the retaining member comprises releasing a length of the belt.

6. The method of claim 1, wherein the predetermined change in the torque or force measured by the sensor is indicative of contact between the plunger and the bung.

7. The method of claim 1, wherein activating the trigger comprises depressing the trigger.

8. The method of claim 1, wherein the trigger comprises a release button.

9. The method of claim 1, wherein activating the trigger comprises axially moving the trigger in a direction of an axis of rotation of the dose setting member.

* * * * *

UNITED STATES PATENT AND TRADEMARK OFFICE
CERTIFICATE OF CORRECTION

PATENT NO. : 10,722,657 B2
APPLICATION NO. : 15/533282
DATED : July 28, 2020
INVENTOR(S) : William Geoffrey Arthur Marsh et al.

It is certified that error appears in the above-identified patent and that said Letters Patent is hereby corrected as shown below:

In the Claims

In Column 19, Line 14 (approx.), Claim 3, after "member," delete "the"

Signed and Sealed this
Twenty-ninth Day of September, 2020

Andrei Iancu
*Director of the United States Patent and Trademark Office*